United States Patent
Herchman, Jr. et al.

(10) Patent No.: US 10,695,219 B2
(45) Date of Patent: Jun. 30, 2020

(54) APPARATUS AND METHOD FOR TREATMENT OF DRY EYE USING RADIO FREQUENCY HEATING

(71) Applicant: ThermiGen, LLC, Southlake, TX (US)

(72) Inventors: Paul R. Herchman, Jr., Grapevine, TX (US); Kevin D. O'Brien, Coppell, TX (US); Gregory L. Almond, Keller, TX (US)

(73) Assignee: THERMIGEN, LLC, Irving, TX (US)

(*) Notice: Subject to any disclaimer, the term of this patent is extended or adjusted under 35 U.S.C. 154(b) by 523 days.

(21) Appl. No.: 15/482,480

(22) Filed: Apr. 7, 2017

(65) Prior Publication Data
US 2017/0333249 A1 Nov. 23, 2017

Related U.S. Application Data

(60) Provisional application No. 62/495,592, filed on Apr. 8, 2016.

(51) Int. Cl.
*A61F 9/007* (2006.01)
*A61N 1/36* (2006.01)

(52) U.S. Cl.
CPC ........ *A61F 9/0079* (2013.01); *A61N 1/36014* (2013.01); *A61N 1/36046* (2013.01)

(58) Field of Classification Search
CPC .................. A61N 1/36014; A61N 1/36046
See application file for complete search history.

(56) References Cited

U.S. PATENT DOCUMENTS

| | | | |
|---|---|---|---|
| 4,823,814 A | 4/1989 | Drogendijk et al. |
| 5,143,063 A | 9/1992 | Fellner et al. |
| 5,413,574 A | 5/1995 | Fugo |
| 5,611,768 A | 3/1997 | Tutrone |
| 5,749,871 A | 5/1998 | Hood et al. |
| 5,771,899 A | 6/1998 | Martelly et al. |
| 5,843,078 A | 12/1998 | Sharkey et al. |
| 5,894,842 A | 4/1999 | Rabin et al. |
| 6,158,435 A | 12/2000 | Dorsey |
| 6,189,535 B1 | 2/2001 | Enhorning |
| 6,241,753 B1 | 6/2001 | Knowlton et al. |
| 6,312,393 B1 | 11/2001 | Abreu |
| 6,383,184 B1 | 5/2002 | Sharkey et al. |
| 6,436,129 B1 | 8/2002 | Sharkey et al. |
| 6,836,688 B2 | 12/2004 | Ingle et al. |
| 6,840,954 B2 | 1/2005 | Dietz et al. |
| 6,882,885 B2 | 4/2005 | Levy et al. |

(Continued)

OTHER PUBLICATIONS

Dmochoski, R. et al. "Transvaginal Radio Frequency Treatment of the Endopelvic Fascia: a Prospective Evaluation for the Treatment of Genuine Stress Urinary Incontinence" J. Urol. vol. 169, Issue 3, pp. 1028-1032 (2003).

(Continued)

*Primary Examiner* — Kaitlyn E Smith
(74) *Attorney, Agent, or Firm* — Hoxie & Associates LLC

(57) ABSTRACT

The present disclosure is related to a treatment probe and method for treating dry eye. The treatment probe may include a thin stainless steel tip, a spacer to ensure proper contact and protect the skin of a patient, a sensor to provide temperature feedback to the power supply providing RF energy to the treatment probe. The treatment focuses on a patient's temple and periorbital area.

14 Claims, 7 Drawing Sheets

(56) References Cited

U.S. PATENT DOCUMENTS

| | | |
|---|---|---|
| 7,094,252 B2 | 8/2006 | Koop et al. |
| 7,167,757 B2 | 1/2007 | Ingle et al. |
| 8,083,787 B2 | 12/2011 | Korb et al. |
| 8,103,355 B2 | 1/2012 | Mulholland et al. |
| 8,187,310 B2 | 5/2012 | Korb et al. |
| 8,187,311 B2 | 5/2012 | Korb et al. |
| 8,317,782 B1 | 11/2012 | Ellman et al. |
| 8,506,558 B2 | 8/2013 | Gertner et al. |
| 8,685,073 B2 | 4/2014 | Korb et al. |
| 8,827,990 B2 | 9/2014 | Van Valen et al. |
| 8,845,630 B2 | 9/2014 | Mehta et al. |
| 8,880,189 B2 | 11/2014 | Lipani |
| 8,915,253 B2 | 12/2014 | Grenon et al. |
| 8,918,181 B2 * | 12/2014 | Ackermann ....... A61N 1/36046 607/53 |
| 8,961,511 B2 | 2/2015 | Parmer et al. |
| 9,017,729 B2 | 4/2015 | Peyman |
| 9,060,843 B2 | 6/2015 | Grenon et al. |
| 9,095,351 B2 | 8/2015 | Sachs et al. |
| 9,095,357 B2 | 8/2015 | Manstein et al. |
| 9,415,235 B2 | 8/2016 | Galen et al. |
| 9,468,774 B2 | 10/2016 | Zarsky et al. |
| 9,719,977 B2 * | 8/2017 | Korb ..................... A61N 1/403 |
| 9,737,712 B2 * | 8/2017 | Franke ................. A61N 1/0546 |
| 2006/0064083 A1 | 3/2006 | Khalaj et al. |
| 2007/0055227 A1 | 3/2007 | Khalaj et al. |
| 2007/0074730 A1 | 4/2007 | Nanduri et al. |
| 2008/0109052 A1 * | 5/2008 | Grenon ............... A61F 9/00772 607/104 |
| 2011/0081333 A1 * | 4/2011 | Shantha ................. A61N 1/328 424/94.62 |
| 2011/0137214 A1 * | 6/2011 | Korb .................. A61F 9/00772 601/3 |
| 2011/0213438 A1 * | 9/2011 | Lima ................... A61N 1/0551 607/42 |
| 2012/0271206 A1 | 10/2012 | Shalev et al. |
| 2013/0110101 A1 | 5/2013 | Van Valen et al. |
| 2013/0172790 A1 | 7/2013 | Badawi |
| 2013/0172829 A1 * | 7/2013 | Badawi ................ A61F 9/0008 604/294 |
| 2014/0073903 A1 * | 3/2014 | Weber ............... A61B 5/04009 606/34 |
| 2014/0148878 A1 | 5/2014 | Khatri et al. |
| 2014/0316310 A1 * | 10/2014 | Ackermann ....... A61N 1/36046 601/46 |
| 2016/0022992 A1 * | 1/2016 | Franke ............... A61N 1/36046 607/59 |
| 2016/0051408 A1 * | 2/2016 | Baerveldt ........... A61F 9/00781 606/6 |
| 2016/0114172 A1 * | 4/2016 | Loudin .............. A61N 1/36046 607/53 |
| 2016/0121118 A1 * | 5/2016 | Franke ................ A61N 1/0546 607/53 |
| 2016/0367806 A1 * | 12/2016 | Kahook ............. A61N 1/36046 |
| 2017/0049619 A1 * | 2/2017 | Kahook ............. A61N 1/36046 |
| 2017/0079834 A1 * | 3/2017 | Badawi ................ A61F 9/0008 |
| 2017/0079840 A1 * | 3/2017 | Badawi ................ A61F 9/0008 |
| 2017/0087009 A1 | 5/2017 | Badawi et al. |
| 2017/0252563 A1 * | 9/2017 | Franke ............... A61N 1/36046 |
| 2017/0340884 A1 * | 11/2017 | Franke ................ A61N 1/0546 |
| 2017/0354818 A1 | 12/2017 | De Toni et al. |
| 2018/0064941 A1 * | 3/2018 | Ackermann ....... A61N 1/36046 |
| 2018/0064942 A1 * | 3/2018 | Franke ............... A61N 1/36046 |
| 2018/0154137 A1 * | 6/2018 | Ackermann ....... A61N 1/36046 |
| 2018/0154161 A1 * | 6/2018 | Ackermann ....... A61N 1/36046 |
| 2018/0193193 A1 * | 7/2018 | Kahook ............. A61F 9/00772 |

OTHER PUBLICATIONS

Zelickson et al., "Histological and Ultrastructural Evaluation of the Effects of a Radiofrequency-Based Nonablative Dermal Remodeling Device", Arch. Dermotol., vol. 140, p. 204-208, (2004).

* cited by examiner

APPARATUS AND METHOD FOR TREATMENT OF DRY EYE USING RADIO FREQUENCY HEATING

RELATED APPLICATIONS

This application claims the benefit under 35 U.S.C. § 120 of U.S. patent application Ser. No. 15/094,814, which has since been converted to U.S. Provisional Application No. 62/495,592, filed on Apr. 8, 2016, which is incorporated herein by reference in its entirety.

FIELD OF THE DISCLOSURE

The present disclosure relates to systems and methods for treatment of evaporative dry eye by radio-frequency heating and reduction to periorbital skin laxity.

BACKGROUND

Meibomian Gland Dysfunction (MGD) can be the result of capped glands, plugged or non-functioning glands or partial or complete gland atrophy. Studies have demonstrated that up to 86% of Dry Eye Syndrome conditions (also known as keratoconjunctivitis sicca and keratitis sicca) are due to evaporative issues connected with MGD. As a result, more emphasis is being placed on MGD treatment for Dry Eye. Current treatments include LipiFlow from Tear Science, MiBo ThermoFlo from Pain Point Medical, hot packs and lid scrubs (commercial to home treatment), yet all of these therapies have drawbacks.

LipiFlow has been proven to work well, but it is expensive with treatments costing over $1800. The functioning unit of the LipiFlow (heating/massaging units) is not intended for reuse. The advantage of LipiFlow is that it massages the lid from the exterior dermal side while heat is simultaneously applied transconjunctivally, making it an effective and efficient treatment. MiBo ThermoFlo applies heat transcutaneously, which is less efficient in terms of altering the consistency of meibomian lipids.

Other methods designed to deliver heat to the lids are applied superficially, e.g., masks, hot washcloths, and others, and have proven to be inadequate for a number of reasons, most specifically due to their inability to bring gland temperature up to required levels, which is estimated to be 40-43° C. (104-109° F.).

ThermiEye™ technology is currently used on the market as a cosmetic skin treatment to tighten skin and reduce wrinkles, under the trade name ThermiSmooth™. It has been shown to be well tolerated and safe for cosmetic use, but has not been considered for treatment of dry eye until now.

This background information is provided to reveal information believed by the applicant to be of possible relevance to the present disclosure. No admission is intended, nor should be construed, that any of the preceding information constitutes prior art against the present disclosure.

SUMMARY OF THE DISCLOSURE

With the above in mind, embodiments of the present disclosure are related to a treatment probe and method for treating dry eye using an RF electrode assembly coupled to the treatment tip, wherein the electrode coupled to the treatment tip is configured to transfer radiofrequency energy to the skin surrounding the eye in such a way that nerve tissue is stimulated and/or strengthened around the eye, reducing MGD. Optionally, a temperature measuring feature is coupled to the electrode assembly, wherein the temperature—measuring feature coupled to the electrode assembly is configured to monitor and regulate electrode and skin temperature, and a protective element that helps to ensure good contact between the electrode and the patient's skin as the electrode is moved across a patient's face.

The ThermiEye™ system delivers radiofrequency energy deep into the skin causing heat to build up where the skin and fat layer meet. The heat escalates to about 42°-45° C., improve Meibomian gland function by stimulating nerve tissue. Additionally, since evaporative dry eye may also be impacted by poor lid-globe apposition, the reduction of tissue laxity and improved elasticity of the tissue surrounding the eye lid may help to further diminish those signs and symptoms classically associated with dry eye.

In various embodiments, the disclosed protocol treats periorbital skin laxity and evaporative dry eye conditions associated with MGD.

In one embodiment, the present disclosure is directed to a method of treatment for dry eye (Method 1), the method comprising directing a radiofrequency energy to target tissue surrounding the eye in an amount sufficient to stimulate but not damage nerve tissue.

1.1 Method 1, wherein the radiofrequency energy is applied through a probe having at least one electrode surface that emits radiofrequency energy.

1.2 Method 1 or 1.1, wherein the radiofrequency energy applied to is low frequency.

1.3 Method 1 or 1.1-1.2, wherein the radiofrequency energy is emitted at a range of about 400 kHz to about 520 kHz; about 430 kHz to about 490 kHz; about 450 kHz to about 470 kHz; about 455 kHz to about 465 kHz; or about 460 kHz.

1.4 Method 1 or 1.1-1.3, wherein the radiofrequency energy is applied in an amount necessary to stimulate nerves to induce secretion of one or more Meibomian glands.

1.5 Method 1 or 1.1-1.4, wherein the radiofrequency energy is applied for a period of time and at a level necessary to raise the surface temperature of target tissue (i.e., epidermis directly above treated dermal tissue) to a temperature between 35 to 47 degrees Celsius.

1.6 Method 1 or 1.1-1.5, wherein the radiofrequency energy is applied for a period of time and at a frequency necessary to raise the surface temperature of target tissue (i.e., epidermis directly above treated dermal tissue) to a temperature between 38 to 45 degrees Celsius.

1.7 Method 1 or 1.1-1.6, wherein the radiofrequency energy is applied for a period of time and at a frequency necessary to raise the surface temperature of target tissue (i.e., epidermis directly above treated dermal tissue) to a temperature between 42 to 44 degrees Celsius.

1.8 Method 1 or 1.4-1.7, wherein the target tissue is heated at between 1 and 5 mm beneath the surface (i.e., between 2 and 2.5 mm beneath the surface).

1.9 Method 1 or 1.1-1.8, wherein the method further comprises applying an electrically conductive gel at the site of the target tissue on a patient.

1.10 Method 1 or 1.1-1.9, wherein the radiofrequency energy is applied to the temple and/or to periorbital tissue adjacent to the eye and/or eyelid.

1.11 Method 1 or 1.1-1.10, wherein the radiofrequency energy is applied to the temple and then is applied to the periorbital tissue adjacent to the eye and/or eyelid.

1.12 Method 1 or 1.1-1.11, wherein the radiofrequency energy is applied for a period of 15 seconds to 20 minutes, a period of 8 minutes to 15 minutes; a period of 8 minutes to 10 minutes; a period of 10 minutes to 12 minutes; or a period of 12 to 15 minutes.

1.13 Method 1 or 1.1-1.12, wherein the radiofrequency energy is not applied to the eyelid.

1.14 Method 1 or 1.1-1.13, further comprising contacting a grounding pad to a patient on an area of the skin removed from the tissue surrounding the eye.

1.15 Method 1 or 1.1-1.14, wherein the radiofrequency energy is applied using a probe that comprises:
  a. an electrically conductive treatment tip positioned at the distal end of a handle,
  b. a cable in contact with the treatment tip and running from the distal end of the handle to the proximal end of the handle, the cable extending from the handle to a power supply providing radio-frequency energy to the tip through the cord, wherein the cord is removable from the power supply
  c. a spacer configured to provide an electrically conductive barrier between the treatment tip and a patient's skin, wherein the treatment tip is adapted to accept the spacer.

1.16 Method 1.15, wherein the cable is permanently affixed within the handle.

1.17 Method 1.15-1.16, wherein the treatment tip comprises a flat distal end configured to contact a patient's skin.

1.18 Method 1.15-1.17, wherein the treatment tip comprises an electrically conductive circumferential sidewall.

1.19 Method 1.18, wherein the electrically conductive circumferential sidewall is continuous with the flat distal end of the treatment tip.

1.20 Method 1.15-1.19, wherein the spacer is shaped to cover the entire treatment tip.

1.21 Method 1.20-1.20, wherein the spacer is shaped to cover the flat distal end and circumferential sidewall of the treatment tip.

1.22 Method 1.15-1.21, wherein the handle comprises an electrically insulative material.

1.23 Method 1.15-1.22, further comprising a temperature sensor (i.e., a thermocouple).

1.24 Method 1.23, wherein the temperature sensor is positioned adjacent the treatment tip.

1.25 Method 1.23-1.24, wherein the temperature sensor abuts an inner surface of the treatment tip.

1.26 Method 1.23-1.24, wherein the temperature sensor is positioned at an outer surface of the treatment tip to facilitate contact with a patient's skin.

1.27 Method 1.15-1.26, wherein the treatment tip has a thickness of about 100 microns.

1.28 Method 1.15-1.27, wherein the treatment tip is between 10 mm and 20 mm wide.

In another embodiment, the present disclosure is directed to radio-frequency emitter (Emitter 2) comprising:
  a. an electrically conductive treatment tip positioned at the distal end of a handle,
  b. a cable in contact with the treatment tip and running from the distal end of the handle to the proximal end of the handle, the cable extending from the handle to a power supply providing radio-frequency energy to the tip through the cord, wherein the cord is removable from the power supply
  c. a spacer configured to provide an electrically conductive barrier between the treatment tip and a patient's skin, wherein the treatment tip is adapted to accept the spacer.

2.1 Emitter 2, wherein the cable is permanently affixed within the handle.

2.2 Emitter 2 or 2.1, wherein the treatment tip comprises a flat distal end configured to contact a patient's skin.

2.3 Emitter 2 or 2.1-2.2, wherein the treatment tip comprises an electrically conductive circumferential sidewall.

2.4 Emitter 2.3, wherein the electrically conductive circumferential sidewall is continuous with the flat distal end of the treatment tip.

2.5 Emitter 2 or 2.1-2.4, wherein the spacer is shaped to cover the entire treatment tip.

2.6 Emitter 2 or 2.1-2.5, wherein the spacer is shaped to cover the flat distal end and circumferential sidewall of the treatment tip.

2.7 Emitter 2 or 2.1-2.6, wherein the handle comprises an electrically insulative material.

2.8 Emitter 2 or 2.1-2.7, further comprising a temperature sensor (i.e., a thermocouple).

2.9 Emitter 2.8, wherein the temperature sensor is positioned adjacent the treatment tip.

2.10 Emitter 2.8-2.9, wherein the temperature sensor abuts an inner surface of the treatment tip.

2.11 Emitter 2.8-2.9, wherein the temperature sensor is positioned at an outer surface of the treatment tip to facilitate contact with a patient's skin.

2.12 Emitter 2 or 2.1-2.11, wherein the treatment tip has a thickness of about 100 microns.

2.13 Emitter 2 or 2.1-2.12, wherein the treatment tip is between 10 mm to 20 mm wide.

DETAILED DESCRIPTION

The present disclosure will now be described more fully hereinafter with reference to the accompanying drawings, in which preferred embodiments of the disclosure are shown. This disclosure may, however, be embodied in many different forms and should not be construed as limited to the embodiments set forth herein. Rather, these embodiments are provided so that this disclosure will be thorough and complete, and will fully convey the scope of the disclosure to those skilled in the art. Those of ordinary skill in the art realize that the following descriptions of the embodiments of the present disclosure are illustrative and are not intended to be limiting in any way. Other embodiments of the present disclosure will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the disclosure. Accordingly, the following embodiments of the disclosure are set forth without any loss of generality to, and without imposing limitations upon, the claimed disclosure.

In this detailed description of the present disclosure, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present disclosure.

Furthermore, in this detailed description, a person skilled in the art should note that quantitative qualifying terms such as "generally," "substantially, "mostly," and other terms are used, in general, to mean that the referred to object, characteristic, or quality constitutes a majority of the subject of the reference. The meaning of any of these terms is dependent upon the context within which it is used, and the meaning may be expressly modified.

Figure 1:
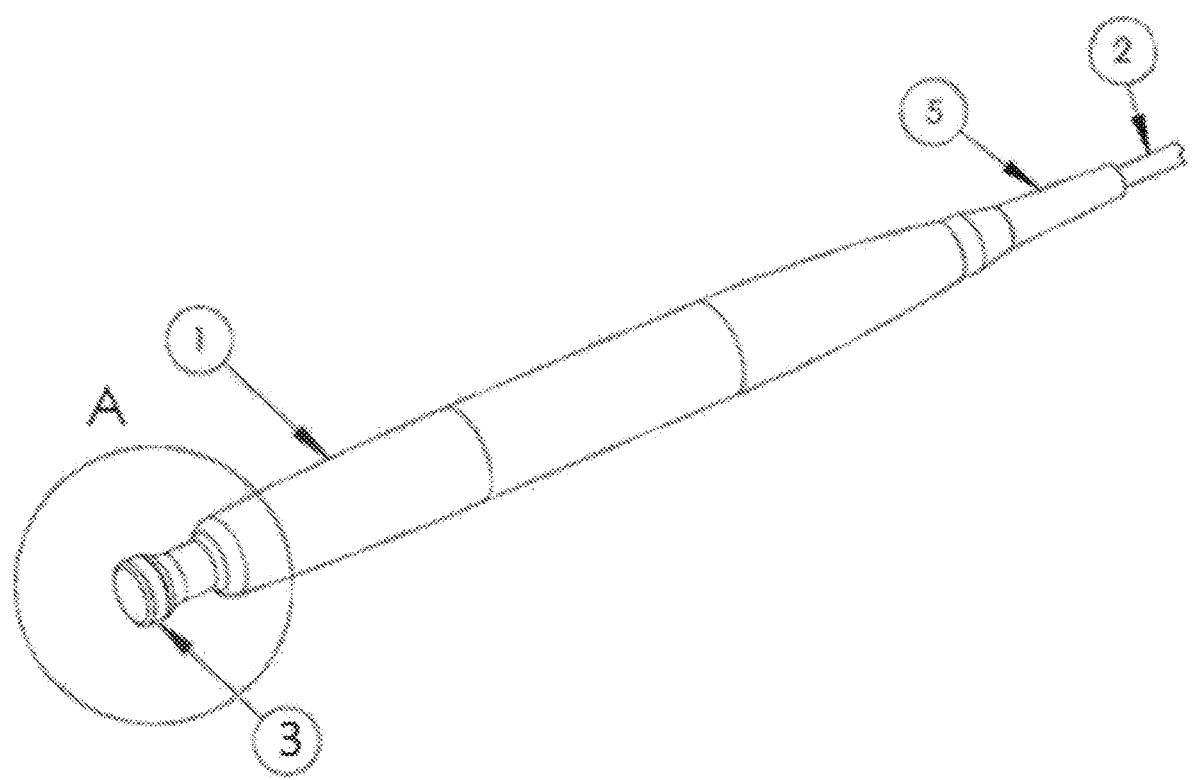
FIG. 1 is an orthogonal view of the user end of an RFE10D Apparatus.
Figure 2:
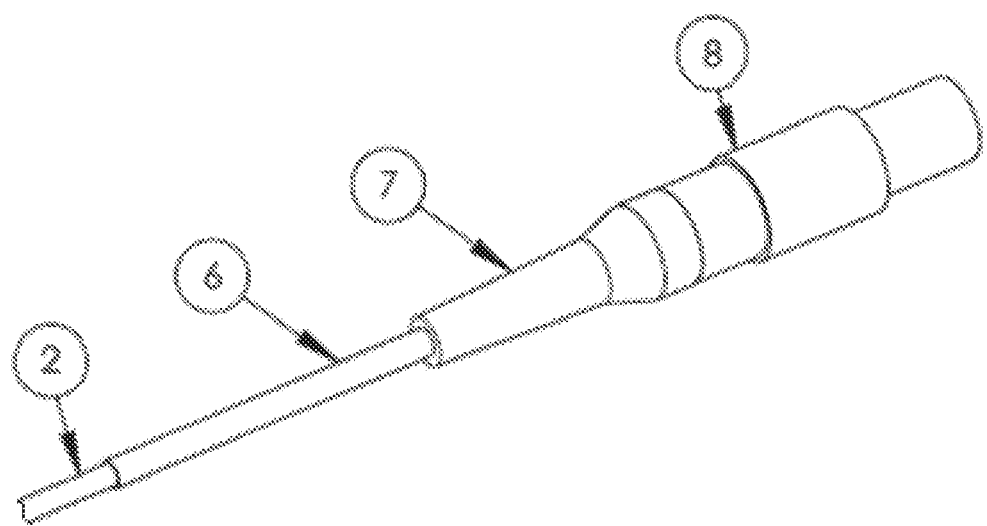
FIG. 2 is an orthogonal view of the connection end of an RFE10D Apparatus.
Figure 3:
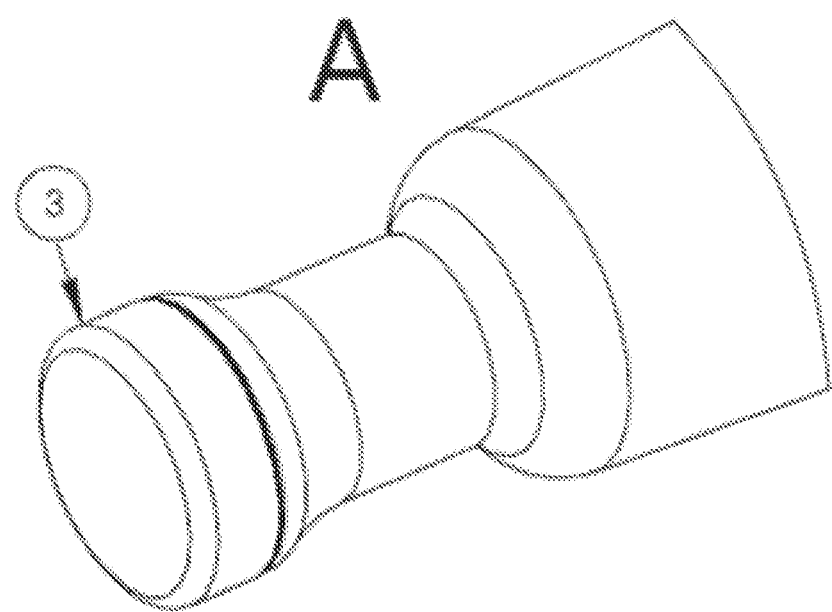
FIG. 3 is a section view of the Apparatus tip as shown in Section A of FIG. 1.

Referring now to FIGS. 1-3, a device, according to an embodiment of the present disclosure disclosed is an RFE-10D RF Electrode Assembly, comprising a Handle 1 with an electrode Tip 3 on it that transfers radio frequency energy into the target tissue only at the location the Tip contacts the tissue. The device receives its the radio frequency energy through a Cable 2 affixed to a Radio Frequency Generator 20 (not shown in FIG. 3). The radio frequency energy travels thru the tissue and exits the body where a large Return Pad 30 is affixed to the patient (shown in FIG. 7).

The treatment probe may be configured to elevate the eye's transconjunctival tissue temperatures to about 40-45° C. to promote tissue contracture.

Tip 3 must contact the tissue, but as shown in FIG. 4A, an optional Spacer 9 composed of a soft, electrically-conductive material may be employed to provide good electrode-patient contact. Use of Spacer 9 helps to ensure the radio frequency energy is evenly distributed over the intended surface area of treatment. Though Spacer 9 shown in FIG. 4A has a particular shape, the electrode could be flat, convex, concave, or other shapes that may be appropriate and comfortable in practice.

The optional Sensor 10 may be any type of thermal sensing device, including but not limited to a thermocouple made part of Spacer 9, in which case Sensor 10 is affixed to the Spacer 9 or Tip 3 so it contacts the patient's skin, or an optical thermal sensing system mounted on the Spacer 9 or Tip 3 that does not make contact, but reads the temperature of the patient's skin. The disclosure is not limited to any particular approach to measuring the skin of the patient. The current embodiment of the disclosure employs a very thin walled cup with the thermometer to its inside wall.

Figure 7:
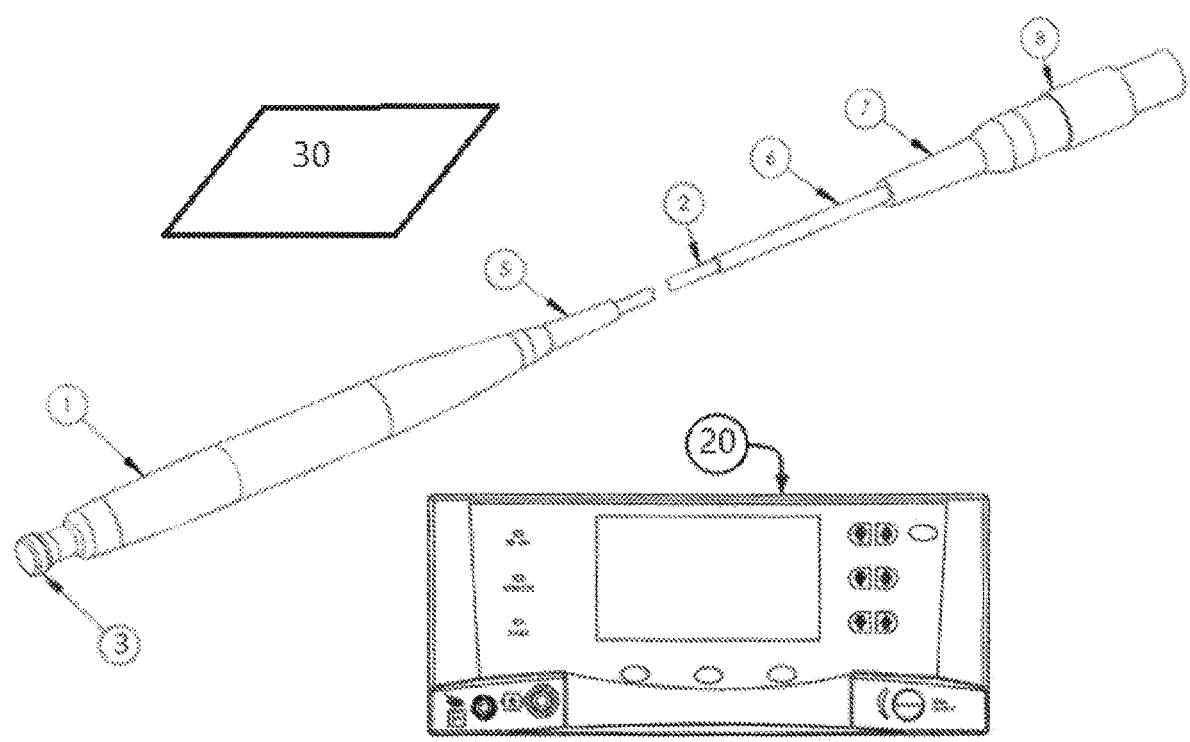
FIG. 7 shows one embodiment of the physical instruments making up the apparatus of the disclosure.

FIG. 7 shows the Emitter is powered by a Power Source 20 conducive to providing energy to the Emitter through the Connector 8 and Cable 2.

Figure 5:
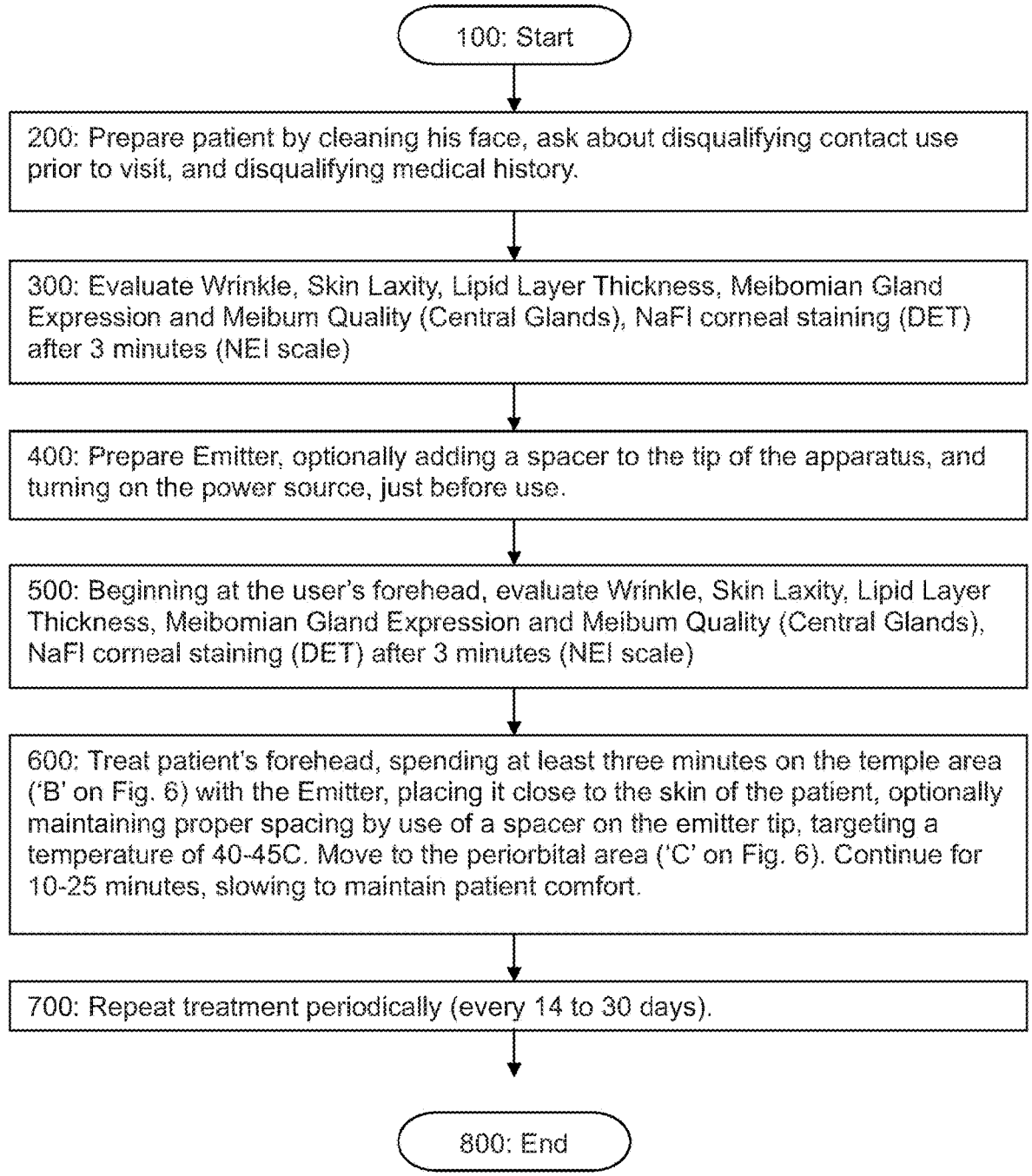
FIG. 5 is a flow chart of the method of treatment.
Figure 6:
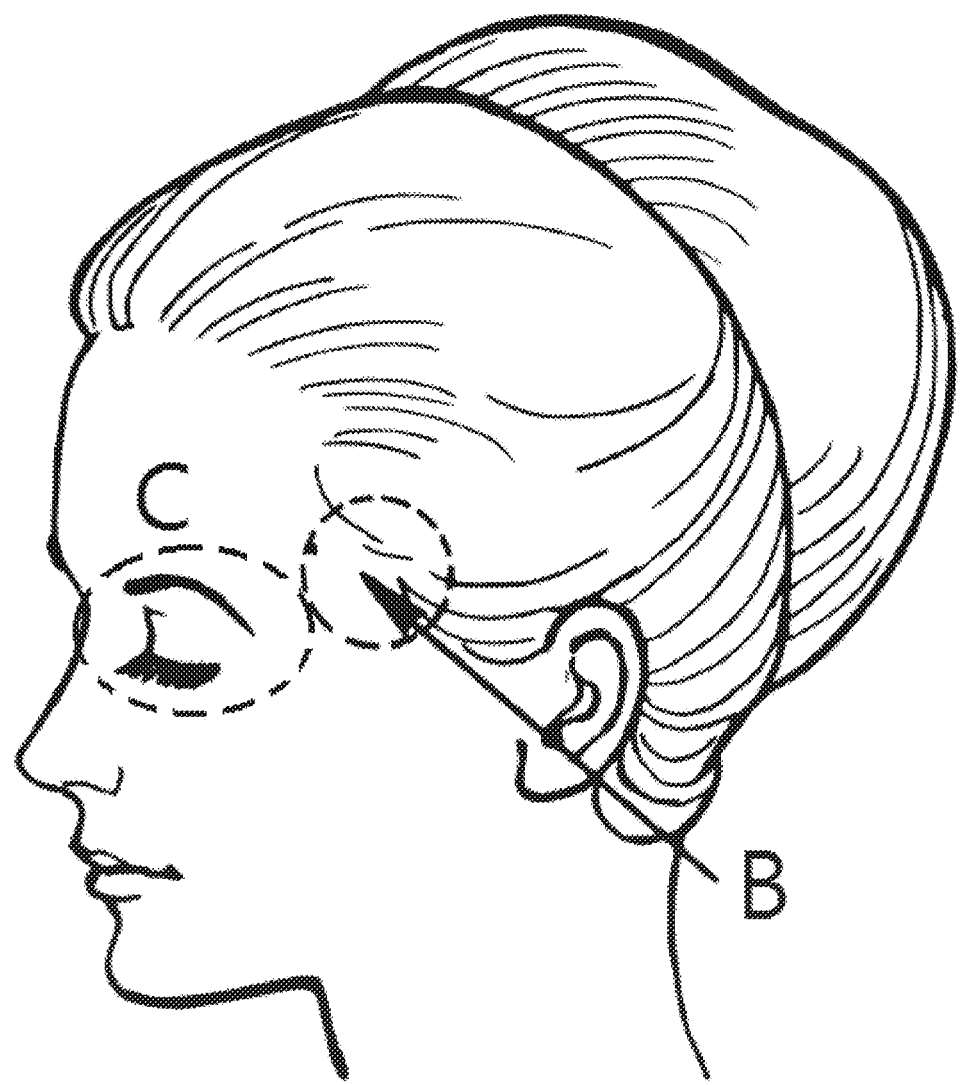
FIG. 6 shows one possible pattern of treatment.

The disclosed Emitter is used to treat the patient around the eye and forehead, using the process disclosed in FIGS. 5 and 6.

In one embodiment, a Control Unit 20 may be configured to deliver additional RF energy so that the temperature at the Sensor 10 can be kept at a desired temperature by the Control Unit's monitoring of the Sensor 10 and applying more or less power to the Emitter.

One of ordinary skill in the art will recognize that there are various algorithms for feedback circuits and each may be used by the Control Unit 20 to accomplish substantially the same result described in the embodiment above. One of ordinary skill in the art will also recognize that a plurality of methods exist to provide energy through heat. In another embodiment of the present disclosure, the RF energy may be replaced with ultrasound, laser heating, and other methods of providing energy through heat.

Figure 4:
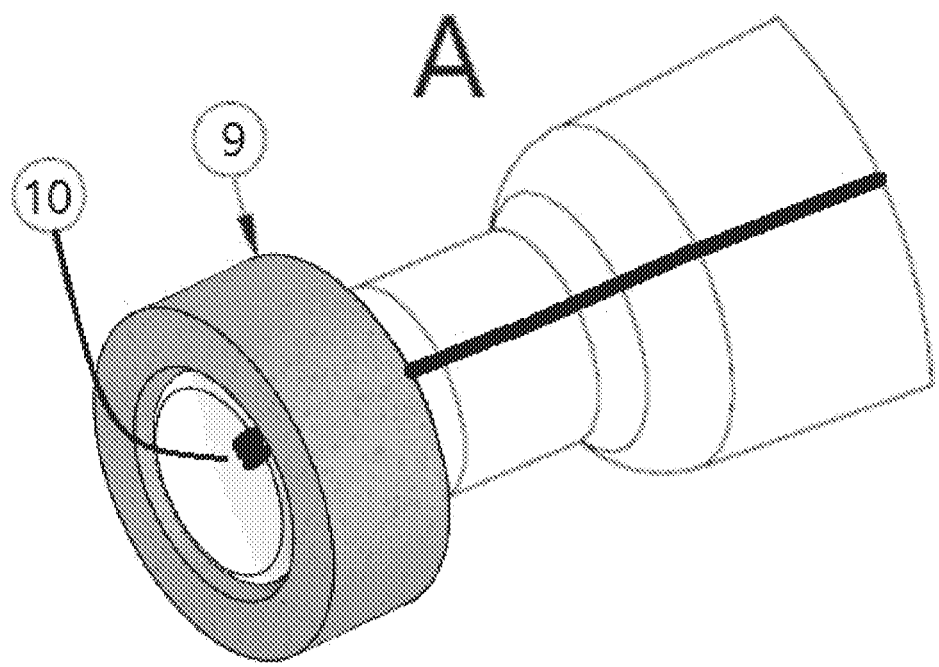
FIG. 4 is a section view the Apparatus tip as shown in Section A of FIG. 1 with an optional electrode construction.

Referring now to FIG. 4, the Emitter can be constructed to accept an optional Spacer 9. Spacer 9 can be constructed to use an adhesive or any number of other methods to be placed on Tip 3. When installed on Tip 3, a user can easily maintain an optimal distance between the Emitter and the patient's skin. Spacer 9 can be washable or disposable, providing easy sanitary practices and separation between patients by changing Spacers 9 between them.

In the disclosed procedure, a user treats the patient's face as indicated in FIGS. 5 and 6. The effect of this treatment is to stimulate nerve growth surrounding the eye, which reduces MGD conditions in the patient.

To accomplish this task most effectively, the nervous tissue around the eye is stimulated by RF energy that traverses a tissue bed. As electric current permeates a tissue layer, ions found within that tissue layer conduct the electric current, increasing kinetic activity of the ions within. Increased ion kinetics and oscillations engender resistive tissue thermogenesis. Thermogenesis may be calculable via the Specific Absorption Rate (hereinafter referred to as "SAR") equation. SAR assesses local electrical conductivity and magnitude of local electric current density generated around an electrode.

A therapeutic benefit of the heat may be localized thermogenesis. An electric field strength generated by the RF energy may be capable of heating tissue in close proximity to the Emitter. With proper power controls, a generated ideal thermal endpoint may occur close to the Emitter. As a result, only the desired specific tissue may be affected.

In some embodiments, the radiofrequency probe disclosed herein is used in a method of stimulating or innervating nerve tissue to treat dry eye (i.e., activate one or more Meibomian glands in a patient).

A medical practitioner or qualified user then powers on power source 20 so as to provide radio frequency energy to treatment tip 3 of the probe. The treatment probe is configured to apply radiofrequency energy to the treatment area of a patient's skin to raise the temperature of the tissue. The radiofrequency energy is applied in an amount necessary to stimulate nerves to induce secretion of one or more Meibomian glands. Notably, the radiofrequency emitted from treatment tip 3 is generally a low frequency, which is intended to provide an amount of energy to the treatment area to specifically stimulate or innervate nerve tissue without damaging surrounding tissue. In various embodiments, the radiofrequency energy emitted has a frequency range of about 400 kHz to about 520 kHz; about 430 kHz to about 490 kHz; about 450 kHz to about 470 kHz; about 455 kHz to about 465 kHz; or about 460 kHz. Application of the radiofrequency energy according to the present method raises the temperature of the target area on a patient's skin from 35° C. to 47° C. In some embodiments, the temperature is raised from 38° C. to a maximum temperature of 42° C. to 45° C. The application of radiofrequency energy to the treatment area on a patient results in dermal tissue heated at a depth of about 1 mm to about 5 mm beneath the outer layer of the epidermis, preferably between 2 mm and 2.5 mm beneath said outer layer of the epidermis.

A medical practitioner may adjust the desired target temperature as necessary according to the needs of the patient. In various embodiments, the probe comprises a temperature sensor 10, which is configured to provide temperature information feedback to power source 20. As discussed herein, in various embodiments power source 20 contains programming logic to automatically cease supply of radiofrequency energy once temperature sensor 10 indicates that a target temperature has been reached. Thus, in methods of use, a medical practitioner may set a target temperature in power source 20, such that during use, upon reaching the target temperature, power source 20 automatically ceases to provide radiofrequency energy to treatment tip 3.

Once a target temperature is set, a medical practitioner brings treatment tip 3 in contact with the temple and/or periorbital tissue surrounding the eye. The probe is oriented relative to the target surface such that the entire surface of the flat distal end of treatment tip 3 is substantially parallel with the patient's skin. An even pressure is applied while moving the treatment tip around the target area at the patient's temple and/or periorbital tissue. This motion is repeated until the target skin temperature is reached. In various embodiments, treatment tip 3 is applied to an area of the patient's skin where nerves in communication with Meibomian glands are located. The radiofrequency energy is applied at such a level and for a period of time so as to stimulate or innervate the nerves involved in Meibomian gland function. While radiofrequency energy may be applied to the periorbital tissue around the eye, it is not applied to the eyelid.

In some embodiments, the treatment area comprises a "C" shape around a patient's eye. The treatment area is continuous from the superior nasal areas located slightly below the eyebrow to the temporal area to the tissue beneath the lower eyelid. In various embodiments, the radiofrequency energy is applied for a period of 15 seconds to 20 minutes, and may be adjusted according to the needs of a particular patient. Thus, in some embodiments, the treatment spans a period of 8 minutes to 15 minutes; a period of 8 minutes to 10 minutes; a period of 10 minutes to 12 minutes; or a period of 12 to 15 minutes.

Generally, the methods of treatment as disclosed herein comprise applying a grounding pad 30 to an area of the patient's skin close to the area being treated. In various embodiments, the area being treated is the periorbital tissue surrounding the eye and/or temple area on a patient's skin. Grounding pad 30 may be disposable and comprise an adhesive surface to adhere to a selected area of the patient's skin. An electrically conductive gel (i.e., coupling gel) is applied to the treatment area of the patient prior to treatment tip 3 being brought into contact with the treatment area. In some embodiments, the gel is an aqueous gel that does not contain glycerin. Preferably, the gel is colorless.

In this Emitter, the Tip 3 has been made much thinner, with embodiments ranging from 10 to 20 mm in width, but only 100 micron thick. This construction is advantageous because it allows for quick response time.

Regulation of tissue temperature may derive from power control circuitry residing in the Power Source 20, which controls the RF power output (and heating) by increasing or decreasing the RF voltage that is transmitted through the cable and to the Tip into the tissue, and monitoring patient tissue temperature.

Some of the illustrative aspects of the present. Disclosure may be advantageous in solving the problems herein described and other problems not discussed which are discoverable by a skilled artisan. While the above description contains much specificity, these should not be construed as limitations on the scope of any embodiment, but as exemplifications of the presented embodiments thereof. Many other ramifications and variations are possible within the teachings of the various embodiments. While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best or only mode contemplated for carrying out this disclosure, but that the disclosure will include all embodiments falling within the scope of the appended claims. Also, the drawings and the description, there have been disclosed exemplary embodiments of the disclosure and, although specific terms may have been employed, they are unless otherwise stated used in a generic and descriptive sense only and not for purposes of limitation, the scope of the disclosure therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

Thus, the scope of the disclosure should be determined by the appended claims and their legal equivalents, and not by the examples given.

A legend of the components discussed in the application and shown on the drawings is as follows:
- 1 Handle
- 2 Cable (Silicon Jacket)
- 3 Tip, 10 mm
- 5 Bend Relief
- 6 Heat Shrink Label Band
- 7 Bend Relief
- 8 Connector
- 9 Spacer (optional)
- 10 Sensor
- 20 Power Source (Radio-Frequency Generator)
- 30 Return Pad

EXAMPLES

Example 1

18 patients aged 45 to 65 with evaporative dry eye and periorbital skin laxity were selected to undergo radiofrequency treatment for dry eye. All selected patients exhibited Meibomian gland dropout. The enrolled patients were evaluated and baseline measures for periorbital skin laxity, presence of wrinkles, dry eye symptoms, ocular surface and extent of Meibomian gland dropout. After the initial evaluation, patients were treated in a randomized eye. Contralateral eyes were left untreated.

Prior to each instance of treatment, patients were given questionnaires to evaluate their apparent symptoms. During treatment, a grounding pad was applied to an area on the skin close to the treatment area (i.e., periorbital tissue). Conduction gel was applied to the skin such that the treatment area was thoroughly coated. The RF generator was powered up, and the treatment temperature was initially set to 38° C. The electrode on the probe was brought into full contact with the patient's skin, and using even pressure and sweeping motions, the temperature of the skin was increased to the target temperature setting (i.e., 38° C.). Once achieved, the temperature was raised by increments of one degree until a target temperature of 42° C. to 45° C. was reached. After treatment, all patients were cleansed and were tested for tear meniscus height, standard dry eye test (DET) using sodium fluorescein strips for tear film break-up time (TFBUT), non-invasive tear break-up time (NITBUT), lipid layer thickness (LLT), and corneal staining.

Treatment according to the method carried out on day 0 was repeated to the randomized eye on days 15 and 30 of the study, and observations were recorded. The contralateral eye was again left untreated. On day 45, no treatment was given, but exit observations were recorded.

A comparison of measures between Visit 1 and the Exit visit on Day 45 showed that the vast majority of patients noticed an improvement in dry eye symptoms over the course of the test period. 9 of the 18 patients showed some incremental improvements with DET TFBUT and 12 of the 18 patients showed improvement in corneal staining. 9 patients demonstrated improvements in LLT, and 10 patients improved with NITBUT, which was measured using a keratograph. These results are especially encouraging since the treatment was not applied to the eye lid at or near the Meibomian glands, but rather on the surrounding tissue removed from the Meibomian glands. There were no noticeable changes to tear meniscus height or Meibomian glands over the course of the study.

Interestingly, the untreated contralateral eyes showed almost equivalent improvements in the same four objective measures LLT, corneal staining, NIBUT and DET TFBUT. This effect was especially unexpected, since no radiofrequency treatment was not applied locally to contralateral tissue.

The results show significant improvement in dry eye symptoms using the described treatment.

We claim:

1. A method of treatment for dry eye, the method comprising application of a radiofrequency energy to target tissue surrounding the eye in an amount sufficient to stimulate but not damage nerve tissue, wherein the radiofrequency energy is applied to the temple and then is applied to the periorbital tissue adjacent to the eye and/or eyelid.

2. A method according to claim 1, wherein the radiofrequency energy is applied through a probe having at least one electrode surface that emits radiofrequency energy.

3. A method according to claim 1, wherein the radiofrequency applied to is low frequency.

4. A method according to claim 1, wherein the radiofrequency energy is emitted at a range of about 400 kHz to about 520 kHz; about 430 kHz to about 490 kHz; about 450 kHz to about 470 kHz; about 455 kHz to about 465 kHz; or about 460 kHz.

5. A method according to claim 1, wherein the radiofrequency energy is applied in an amount necessary to stimulate nerves to induce secretion of one or more Meibomian glands.

6. A method according to claim 1, wherein the radiofrequency energy is applied for a period of time and at a level necessary to raise the surface temperature of the target tissue to a temperature between 35 to 47 degrees Celsius.

7. A method according to claim 6, wherein the radiofrequency energy is applied for a period of time and at a frequency necessary to raise the surface temperature of the target tissue to a temperature between 38 to 45 degrees Celsius.

8. A method according to claim 7, wherein the radiofrequency energy is applied for a period of time and at a frequency necessary to raise the surface temperature of the target tissue to a temperature between 42 to 44 degrees Celsius.

9. A method according to claim 1, wherein the target tissue is heated at between 1 and 5 mm beneath the surface of the target tissue.

10. A method according to claim 9, wherein the method further comprises applying an electrically conductive gel at the site of the target tissue on a patient.

11. A method according to claim 1, wherein the radiofrequency energy is applied for a period of 15 seconds to 20 minutes, a period of 8 minutes to 15 minutes; a period of 8 minutes to 10 minutes; a period of 10 minutes to 12 minutes; or a period of 12 to 15 minutes.

12. A method according to claim 1, wherein the radiofrequency energy is not applied to the eyelid.

13. A method according to claim 1, further comprising contacting a grounding pad to a patient on an area of the skin removed from the tissue surrounding the eye.

14. A method according to claim 1, wherein the radiofrequency energy is applied using a probe that comprises:
 a. an electrically conductive treatment tip positioned at the distal end of a handle,
 b. a cable in contact with the treatment tip and running from the distal end of the handle to the proximal end of the handle, the cable extending from the handle to a power supply providing radio-frequency energy to the tip through the cord, wherein the cord is removable from the power supply
 c. a spacer configured to provide an electrically conductive barrier between the treatment tip and a patient's skin, wherein the treatment tip is adapted to accept the spacer.

* * * * *